United States Patent [19]

Matsuno et al.

[11] 4,390,723
[45] Jun. 28, 1983

[54] PROCESS FOR PRODUCING HYDROXYPHENYL ALIPHATIC ACID DERIVATIVES

[75] Inventors: Masahiro Matsuno, Fuji; Yasushi Higuchi; Yutaka Ohishi, both of Shizuoka; Yoshiki Nakayama, Shimizu; Chihiro Yazawa, Yokohama, all of Japan

[73] Assignee: Ihara Chemical Industry Co., Ltd., Tokyo, Japan

[21] Appl. No.: 290,305

[22] Filed: Aug. 5, 1981

[30] Foreign Application Priority Data

Aug. 29, 1980 [JP] Japan .............................. 55/118401
Feb. 12, 1981 [JP] Japan .............................. 56/19510

[51] Int. Cl.$^3$ .................................................. C07C 65/01
[52] U.S. Cl. ...................................... 562/478; 252/431 N
[58] Field of Search .......................................... 562/478

[56] References Cited

PUBLICATIONS

Lisitsyn, V. N. et al., JOCS (USSR), vol. 7, 1971, pp. 2666–2668.
J. Morg. Nucl. Chem., 1963, vol. 25, pp. 29–35.

*Primary Examiner*—Paul J. Killos
*Attorney, Agent, or Firm*—Oblon, Fisher, Spivak, McClelland & Maier

[57] ABSTRACT

A catalyst of bis(8-quinolinolate) copper (II) complex having the formula

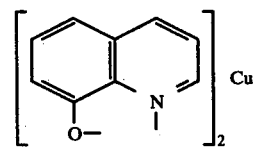

which is used for producing a hydroxyphenyl aliphatic acid derivative having the formula

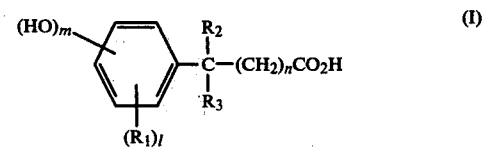

wherein $R_1$ represents hydrogen atom, a lower alkyl group, a lower alkoxy group, hydroxy group or a lower alkylcarbonyl group; $R_2$ and $R_3$ are the same or different and respectively represent hydrogen atom or a lower alkyl group; and m is 1 or 2; l is 0, 1 or 2; n is 0, 1 or 2; by reacting a halophenyl aliphatic acid derivative having the formula

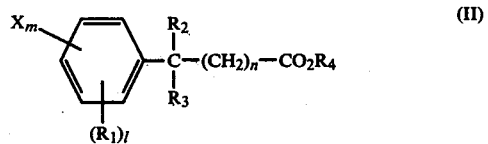

wherein $R_1$, $R_2$, $R_3$, m, l and n are defined above and $R_4$ represents hydrogen atom or a monovalent hydrocarbon moiety; and X represents a halogen atom, with a base.

8 Claims, No Drawings

PROCESS FOR PRODUCING HYDROXYPHENYL ALIPHATIC ACID DERIVATIVES

BACKGROUND OF THE INVENTION

1. Field of the Invention

The present invention relates to a process for producing a hydroxyphenyl aliphatic acid derivative having the formula

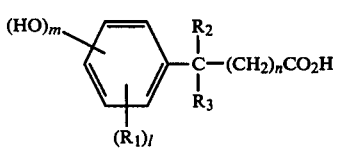

wherein $R_1$ represents hydrogen atom, a lower alkyl group, a lower alkoxy group, hydroxy group or a lower alkylcarbonyl group; $R_2$ and $R_3$ are the same or different and respectively represent hydrogen atom or a lower alkyl group; and m is 1 or 2; l is 0, 1 or 2; n is 0, 1 or 2; by reacting a halophenyl aliphatic acid derivative having the formula

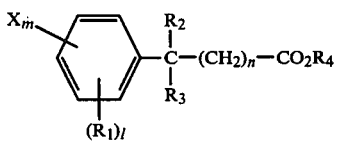

wherein $R_1$, $R_2$, $R_3$, m, l and n are defined above and $R_4$ represents hydrogen atom or a monovalent hydrocarbon moiety; and X represents a halogen atom, with a base and a catalyst used for the process.

2. Description of the Prior Art

The hydroxyphenyl aliphatic acid derivatives especially acetic acid derivatives are known to be effective as intermediates for cholekinetics and agricultural chemicals.

Certain processes for producing hydroxyphenyl aliphatic acid derivatives have been known as follows:

a process for producing 2-hydroxyphenylacetic acid by converting 2-methoxyacetophenone into 2-methoxyphenylacetic acid and treating the product with hydrobromic acid as described in J. Org. Chem. 11 (1946) p. 798;

a process for producing hydroxyphenylacetic acid by reducing nitrophenylacetic acid and diazotating and hydrolyzing the resulting aminophenylacetic acid, as described in J. Chem. Soc. (London) 1948, p. 150;

a process for producing hydroxyphenylacetic acid by hydrolyzing 2-bromophenylacetic acid in an aqueous solution of morpholine in the presence of bis(ethylenediamine) copper (II) salt, as described in J.O.C. (USSR) 1971, p. 2666–2668; and a process for producing 2-hydroxyphenylacetic acid by reacting a halophenylacetic acid such as 2-chlorophenylacetic acid with an alkali metal hydroxide in the presence of a metallic copper or a copper salt, as described in Japanese Unexamined Patent Publication No. 4870/1972.

Among the known processes, the process of Japanese Unexamined Patent Publication No. 4870/1972 is superior to others in view of high yield of 2-hydroxyphenylacetic acid. In the specification, the yield of 2-hydroxyphenylacetic acid is in a range of 82 to 95%.

However, the reaction is performed at high temperature such as 220° to 250° C. under high temperature such as 20 to 60 atom. Therefore, this process is not advantageous as the industrial process.

SUMMARY OF THE INVENTION

It is an object of the present invention to provide a process for producing a hydroxyphenyl aliphatic acid derivative having the formula (I) at high yield under a mild condition of a temperature and a pressure which are milder than those of the conventional process.

It is another object of the present invention to provide a catalyst used for the process for producing the hydroxyphenyl aliphatic acid derivative having the formula (I).

The foregoing objects of the present invention have been attained by providing a catalyst of bis(8-quinolinolate) copper (II) complex having the formula

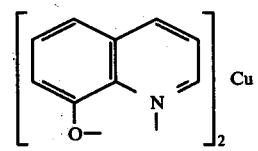

which is used for producing a hydroxyphenyl aliphatic acid derivative having the formula

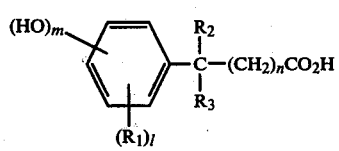

wherein $R_1$ represents hydrogen atom, a lower alkyl group, a lower alkoxy group, hydroxy group or a lower alkylcarbonyl group; $R_2$ and $R_3$ are the same or different and respectively represent hydrogen atom or a lower alkyl group; and m is 1 or 2; l is 0, 1 or 2; n is 0, 1 or 2; by reacting a halophenyl aliphatic acid derivative having the formula

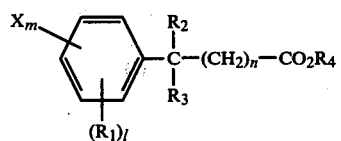

wherein $R_1$, $R_2$, $R_3$, m, l and n are defined above and $R_4$ represents hydrogen atom or a monovalent hydrocarbon moiety; and X represents a halogen atom, with a base.

The other feature of the present invention is to provide a process for producing a hydroxyphenyl aliphatic acid derivative having the formula (I) by using the catalyst of bis(8-quinolinolate) copper (II) complex having the formula

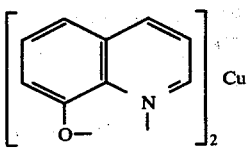

DETAILED DESCRIPTION OF THE PREFERRED EMBODIMENTS

Bis(8-quinolinolate) copper (II) complex used as the catalyst can be easily produced by reacting 8-quinolinol ($C_9H_7NO$) with a copper (II) salt such as $CuSo_4.5H_2O$, $CuCl_2$, $Cu(NO_3)_2.3H_2O$, $Cu(ClO_4)_2.6H_2O$ and $Cu(C_2H_3O_2)_2.H_2O$ in water and/or methanol or ethanol as described in J. C. Fanning, H. B. Jonassen; J. Inorg. Nucl. Chem. 1963, Vol. 25 p. 29–35.

A desired molar ratio of the catalyst to the halophenyl aliphatic acid is depending upon a reaction temperature, a reaction time, kinds of a halophenyl aliphaic acid derivative and a starting material and is usually in a range of 0.001 to 0.3 preferably 0.01 to 0.2.

The catalyst used in the hydrolyzing reaction can be recovered and reused by neutralizing the reaction mixture by adding an acid to precipitate the catalyst in the crystalline form after the reaction and separating the crystal by a filtration.

The halophenyl aliphatic acid derivatives having the formula (II) used as the starting material in the process of the present invention can be the compounds having a halogen atom as X. Thus, the compounds having chlorine atom as X are especially important starting materials used in the process of the present invention because the chlorine substituent group is not easily hydrolyzed except the condition of a high temperature. The halophenyl aliphatic acid derivatives can be free acids ($R_4=H$) or esters ($R_4=$hydrocarbon moiety).

Suitable hydrocarbon moieties as $R_4$ include alkyl groups such as methyl, ethyl and n-butyl groups; and aralkyl groups such as benzyl and phenethyl groups.

Suitable halophenyl aliphatic acid derivatives include 2-chlorophenylacetic acid, 3-chlorophenylacetic acid, 4-chlorophenylacetic acid, 2-(4'-chlorophenyl)-3-methylbutanoic acid, 4-chloro-3-methylphenylacetic acid, 3-chloro-4,6-dimethylphenylacetic acid, 3-chloro-4,5-dimethylphenylacetic acid, 2-(4'-chloro-3'-methylphenyl) butanoic acid, 2-(2'-chloro-4'-methylphenyl)-2-methylpropanoic acid, 2-chloro-3-methoxyphenylacetic acid, 4-chloro-3-methoxyphenylacetic acid, 3-chloro-6-methoxyphenylacetic acid, 2-chloro-5-acetylphenylacetic acid, 2-chloro-4-hydroxyphenylacetic acid, 2,5-dichlorophenylacetic acid, 3-(2'-chlorophenyl) propanoic acid, 4-(4'-chlorophenyl) butanoic acid and also methyl, ethyl, n-propyl, isopropyl, n-butyl, isobutyl, n-octyl, benzyl, α-phenetyl or β-phenetyl esters thereof.

Suitable bases used for reacting with the halophenyl aliphatic acid derivative, include sodium hydroxide, potassium hydroxide, sodium carbonate and potassium carbonate.

A molar ratio of the base to the halophenyl aliphatic acid derivative is in a range of 1 to 10 preferably 2 to 7. The base is usually used in the form of an aqueous solution. A concentration of the base is 50 wt.% or less preferably in a range of 5 to 30 wt.%. When the concentration of the base is higher than 50 wt.%, it is difficult to perform a uniform mixing of the reaction mixture to cause a heterogeneous reaction.

The hydrolyzing reaction is usually performed at a reaction temperature of 100° to 300° C. preferably 150° to 250° C. The reaction time is reversely proportional to the reaction temperature. At a relatively low temperature of 150° to 170° C., the reaction time is usually several hours or longer. At a relatively high temperature of 230° to 250° C., the reaction time is usually 2 hours or shorter. The reaction time is decided depending upon the reaction temperature and kinds of the catalyst and the starting material.

The hydrolyzing reaction is preferably performed under a spontaneous pressure in an autoclave. The spontaneous pressure of about 4 to 35 kg/cm² is applied at the reaction temperature of 150° to 250° C.

The present invention will be illustrated by certain examples and references which are provided for purposes of illustration only and are not intended to be limiting the invention.

EXAMPLE 1

Into an autoclave, 124 g. (0.4 mol) of 13% aqueous solution of sodium hydroxide, 17.1 g. (0.1 mol) of 2-chlorophenylacetic acid and 3.52 g. (0.01 mol) of bis(8-quinolinolate) copper (II) complex were charged. A reaction was performed at 170° C. under a spontaneous pressure for 2 hours. The pressure was 6.5–7 kg/cm².

After the reaction, the reaction mixture was cooled and neutralized by adding concentrated hyrochloric acid and the resulting bis(8-quinolinolate) copper was separated by a filtration. The resulting filtrate was concentrated under a reduced pressure, and then concentrated hydrochloric acid was added and the precipitated crystal was separated by a filtration and washed with water and dried to obtain 14.4 g. of a white platy crystal of 2-hydroxyphenylacetic acid having a melting point of 142°–144° C. (yield of 95%).

REFERENCE 1

Into an autoclave, 124 g. (0.4 mol) of 13% aqueous solution of sodium hydroxide, 17.1 g. (0.1 mol) of 2-chlorophenylacetic acid and 2.5 g. (0.01 mol) of cupric sulfate ($CuSO_4.5H_2O$) were charged. A reaction was performed at 170° C. under a spontaneous pressure for 6 hours. The pressure was 6.5–7 kg/cm².

After the reaction, the reaction mixture was cooled and neutralized by adding concentrated hydrochloric acid and the precipitated crystal was separated by a filtration and washed with water and dried to obtain 3.8 g. of a white platy crystal of 2-hydroxyphenylacetic acid having a melting point of 142°–144° C. (yield of 25%).

REFERENCE 2

Into an autoclave, 124 g. (0.4 mol) of 13% aqueous solution of sodium hydroxide, 17.1 g. (0.1 mol) of 2-chlorophenylacetic acid, 0.42 g. (0.0067 mol) of copper powder and 0.44 g. (0.0033 mol) of cupric chloride were charged. A reaction was performed at 170° C. under a spontaneous pressure for 6 hours. The pressure was 6.5–7 kg/cm².

After the reaction, the reaction mixture was cooled and the copper powder was separated by a filtration and the resulting filtrate was concentrated under a reduced pressure and was neutralized by adding concentrated hydrochloric acid to be acidic and the precipitated crystal was separated by a filtration and washed with water and dried to obtain a white platy crystal of 2-hydroxyphenylacetic acid having a melting point of 142°–144° C. (yield of 26%).

EXAMPLE 2

In accordance with the process of Example 1, a reaction of 4-chlorophenylacetic acid with sodium hydroxide was performed in the presence of bis(8-quinolinolate) copper (II) complex. The reaction time was changed to 6 hours and the other reaction condition and the amounts of the reagents were the same as those of Example 1. The reaction mixture was treated by the same process to obtain 14.6 g. of a white platy crystal of 4-hydroxyphenylacetic acid having a melting point of 148°–149° C. (yield of 96%).

EXAMPLE 3

In accordance with the process of Example 1, a reaction of 2-(4'-chlorophenyl)-3-methylbutanoic acid with sodium hydroxide was performed in the presence of bis(8-quinolinolate) copper (II) complex. The amount of 2-(4'-chlorophenyl)-3-methylbutanoic acid was changed to 21.2 g. (0.1 mol) and the other condition was the same as that of Example 1. The reaction mixture was treated by the same process to obtain 19.2 g. of a white platy crystal of 2-(4'-hydroxyphenyl)-3-methylbutanoic acid having a melting point of 167.5°–168° C. (yield of 99%).

The process was repeated except varying the reaction temperature (the spontaneous pressure) and the reaction time. The results are as follows:

| Reaction temperature (°C.) | Reaction pressure (kg/cm²) | Reaction time (hr.) | Yield (%) |
|---|---|---|---|
| 170 | 6.5–7 | 6.0 | 99 |
| 200 | 13–14 | 3.0 | 89 |
| 235 | 25–27 | 2.0 | 86.7 |

EXAMPLE 4

In accordance with the process of Example 3, 2-(4'-hydroxyphenyl)-3-methylbutanoic acid was produced. The reaction temperature and the reaction pressure was respectively set to 170° C. and 6.5–7 kg/cm². The amount of the catalyst and the reaction time were varied as follows: The yields were as follows:

| Amount of catalyst (mol) | Reaction time (hr.) | Yield (%) |
|---|---|---|
| 0.02 | 4.0 | 99 |
| 0.01 | 6.0 | 99 (Exp. 3) |
| 0.007 | 6.0 | 97 |
| 0.005 | 10.0 | 91 |
| 0.002 | 17.0 | 86 |

EXAMPLE 5

In accordance with the process of Example 1, a reaction of methyl 4-chlorophenylacetate with sodium hydroxide was performed in the presence of bis(8-quinolinolate) copper (II) complex. The amount of methyl 4-chlorophenylacetate was 18.5 g. (0.1 mol) and the amount of 13% aqueous solution of sodium hydroxide was 185 g. (0.6 mol) and the other condition was the same as that of Example 1. The reaction mixture was treated by the same process to obtain 14.6 g. of a white platy crystal of 4-hydroxyphenylacetic acid having a melting point of 148°–149° C. (yield of 96%).

REFERENCES 4 AND 5

In accordance with the process of Example 3, 2-(4'-chlorophenyl)-3-methylbutanoic acid was hydrolyzed. The reaction temperature and the reaction pressure were respectively 200° C. and 13–14 kg/cm². The following catalyst was respectively used.

(i) 0.0067 mol of copper powder+0.0033 mol of cupric chloride (total: 0.01 mol catalyst described in Japanese Unexamined Patent Publication 4870/1972; Reference 4).

(ii) 0.1 mol of bis(ethylenediamine) copper sulfate (catalyst described in J.O.C. (USSR) 1971, p. 2666–2668; Reference 5).

The results of the reaction were as follows:

| | Catalyst | Reaction time (hr) | Yield (%) |
|---|---|---|---|
| Reference 4 | Cu + CuCl₂ | 7.0 | 35.3 |
| Reference 5 | [Cu(en)₂]SO₄ | 10.0 | 45.9 |
| Example 3 | (8-quinolate)₂ Cu | 3.1 | 89.0 |

Note:
en: ethylenediamine

EXAMPLE 6

Into a autoclave, 124 g. (0.4 mol) of 13% aqueous solution of sodium hydroxide, 18.4 g. (0.1 mol) of 4-chloro-3-methylphenylacetic acid and 3.51 g. (0.01 mol) of bis(8-quinolinolate) copper (II) complex were charged. A reaction was performed at 170° C. under a spontaneous pressure for 2 hours. The pressure was 6.5–7 kg/cm².

After the reaction, the reaction mixture was cooled and neutralized by adding concentrated hydrochloric acid and the resulting bis(8-quinolinolate) copper was separated by a filtration. The filtrate was concentrated under a reduced pressure and concentrated hydrochloric acid was added and the precipitated crystal was separated by a filtration and washed with water and dried to obtain 15.8 g. of white platy crystal of 4-hydroxy-3-methylphenylacetic acid having a melting point of 109°–110° C. (yield of 95.4%).

REFERENCE 6

Into an autoclave, 124 g. (0.4 mol) of 13% aqueous solution of sodium hydroxide, 18.4 g. (0. 1 mol) of 4-chloro-3-methylphenylacetic acid, 2.5 g. (0.01 mol) of cupric sulfate (CuSO₄.5H₂O) were charged. A reaction was performed at 170° C. under a spontaneous pressure for 6 hours. The pressure was 6.5–7 kg/cm².

After the reaction, the reaction mixture was cooled and neutralized by adding concentrated hydrochloric acid and the precipitated crystal was separated by a filtration and washed with water and dried to obtain 4.1 g. of a white platy crystal of 4-hydroxy-3-methylphenylacetic acid having a melting point of 109°–110° C. (yield of 25%).

REFERENCE 7

Into an autoclave, 124 g. (0.4 mol) of 13% aqueous solution of sodium hydroxide, 18.4 g. (0.1 mol) of 4-chloro-3-methylphenylacetic acid, 0.42 g. (0.0067 mol) of copper powder and 0.44 g. (0.0033 mol) of cupric chloride were charged. A reaction was performed at 170° C. under a spontaneous pressure for 6 hours. The pressure was 6.5-7 kg/cm².

After the reaction, the reaction mixture was cooled and the insoluble copper powder was separated by a filtration. The filtrate was concentrated under a reduced pressure and acidified by adding concentrated hydrochloric acid. The precipitated crystal was separated by a filtration and washed with water and dried to obtain 4.3 g. of a white platy crystal of 4-hydroxy-3-methylphenylacetic acid having a melting point of 109°-110° C. (yield of 26%).

EXAMPLE 7

In accordance with the process of Example 6, a reaction of 2-(4'-chloro-3'-methylphenyl)butanoic acid with sodium hydroxide was performed in the presence of bis(8-quinolinolate) copper (II) complex. The amount of 2-(4'-chloro-3'-methylphenyl) butanoic acid was varied to 21.2 g. (0.1 mol) and the other condition was the same as that of Example 6. The reaction mixture was treated by the same process to obtain 19.2 g. of a white platy crystal of 2-(4'-hydroxy-3'-methylphenyl) butanoic acid having a melting point of 82°-85° C. (yield of 99%).

The process was repeated except varying the reaction temperature (the spontaneous pressure) and the reaction time. The results are as follows:

| Reaction temperature (°C.) | Reaction pressure (kg/cm²) | Reaction time (hr.) | Yield (%) |
|---|---|---|---|
| 170 | 6.5-7 | 6.0 | 95 |
| 200 | 13-14 | 3.0 | 92 |
| 235 | 25-27 | 2.0 | 80 |

EXAMPLE 8

In accordance with the process of Example 7, 2-(4'1-hydroxy-3'-methylphenyl) butanoic acid was produced. The reaction temperature and the reaction pressure were respectively set to 170° C. and 6.5-7 kg/cm². The amount of the catalyst and the reaction time were varied as follows: The yields were as follows:

| Amount of catalyst (mol) | Reaction time (hr.) | Yield (%) |
|---|---|---|
| 0.02 | 4.0 | 95 |
| 0.01 | 6.0 | 95 (Exp. 7) |
| 0.007 | 6.0 | 96 |
| 0.005 | 10.0 | 94 |
| 0.002 | 17.0 | 93 |

EXAMPLES 9-19

In accordance with the process of Example 6 except varying kinds of the halophenyl aliphatic acid derivative and the catalyst each reaction and purification were carried out. The results are shown in Table.

TABLE

| Halophenyl aliphatic acid derivative | Hydroxyphenyl aliphatic acid derivative | Melting point (°C.) | Yield (%) |
|---|---|---|---|
| 9 3-chloro-4,6-dimethyl-phenylacetic acid | 3-hydroxy-4,6-dimethyl-phenylacetic acid | 155-157 | 96 |
| 10 3-chloro-4,5-dimethyl-phenylacetic acid | 3-hydroxy-4,5-dimethyl-phenylacetic acid | 145.5-146.5 | 94 |
| 11 2-(2'-chloro-4'-methyl-phenyl)-2-methyl-propanoic acid | 2-(2'-hydroxy-4'-methyl-phenyl)-2-methyl-propanoic acid | 106-108 | 95 |
| 12 2-chloro-3-methoxy-phenylacetic acid | 2-hydroxy-3-methoxy-phenylacetic acid | 120-122.5 | 96 |
| 13 4-chloro-3-methoxy-phenylacetic acid | 4-hydroxy-3-methoxy-phenylacetic acid | 137-139 | 94 |
| 14 3-chloro-6-methoxy-phenylacetic acid | 3-hydroxy-6-methoxy-phenylacetic acid | 119-120 | 96 |
| 15 2-chloro-5-acetyl-phenylacetic acid | 2-hydroxy-5-acetyl-phenylacetic acid | 184-187 | 92 |
| 16 2-chloro-4-hydroxy-phenylacetic acid | 2,4-dihydroxyphenyl-acetic acid | 112-114 | 90 |
| 17 2,5-dichlorophenyl-acetic acid | 2,5-dihydroxyphenyl-acetic acid | 146-147 | 90 |
| 18 3-(2'-chlorophenyl)propanoic acid | 3-(2'-hydroxyphenyl)propanoic acid | 41-42 | 96 |
| 19 4-(4'-chlorophenyl)butanoic acid | 4-(4'-hydroxyphenyl)butanoic acid | 59-60 | 96 |

We claim:

1. In a process for producing a hydroxyphenyl aliphatic acid derivative having the formula

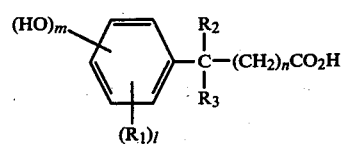

wherein $R_1$ represents hydrogen atom, a lower alkyl group, a lower alkoxy group, hydroxy group or a lower alkylcarbonyl group; $R_2$ and $R_3$ are the same or different and respectively represent hydrogen atom or a lower alkyl group; and m is 1 or 2; l is 0, 1 or 2; n is 0, 1 or 2; by reacting a halophenyl aliphatic acid derivative having the formula

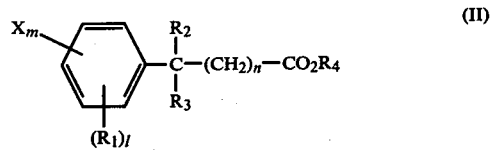

wherein $R_1$, $R_2$, $R_3$, m, l and n are defined above and $R_4$ represents hydrogen atom or a monovalent hydrocarbon moiety; and X represents a halogen atom, with a base an improvement characterized by reacting them in the presence of a catalyst of bis(8-quinolinolate) copper (II) complex having the formula

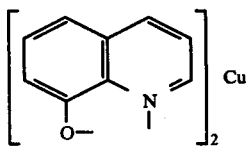

2. The process according to claim 1 wherein a hydroxyphenylacetic acid derivative having the formula

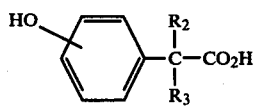

wherein $R_2$ and $R_3$ are defined in claim 1 is produced by reacting a halophenylacetic acid derivative having the formula

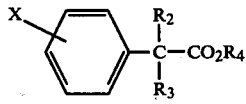

wherein $R_2$, $R_3$, $R_4$ and X are defined in claim 1, with a base.

3. The process according to claim 1 or 2 wherein a molar ratio of the catalyst to the halophenyl aliphatic acid derivative is in a range of 0.001 to 0.3.

4. The process according to claim 1 or 2 wherein a reaction temperature is in a range of 100° to 300° C.

5. The process according to claim 1 or 2 wherein the base is at least one of sodium hydroxide, potassium hydroxide, sodium carbonate and potassium carbonate and a molar ratio of the base to the halophenyl aliphatic acid derivative is in a range of 1 to 10.

6. The process according to claim 1 or 2 wherein halogen atom of the halophenyl aliphatic acid derivative is chlorine atom.

7. The process according to claim 2 wherein the halophenylacetic acid derivative is 2-chlorophenylacetic acid, 4-chlorophenylacetic acid, 2-(4'-chlorophenyl)-3-methylbutanoic acid or an ester thereof.

8. The process according to claim 1 wherein the halophenyl aliphatic acid derivative is 2-chlorophenylacetic acid, 3-chlorophenylacetic acid, 4-chlorophenylacetic acid, 2-(4'-chlorophenyl)-3-methylbutanoic acid, 4-chloro-3-methylphenylacetic acid, 3-chloro-4,6-dimethylphenylacetic acid, 3-chloro-4,5-dimethylphenylacetic acid, 2-(4'-chloro-3'-methylphenyl) butanoic acid, 2-(2'-chloro-4'-methylphenyl)-2-methylpropanoic acid, 2-chloro-3-methoxyphenylacetic acid, 4-chloro-3-methoxyphenylacetic acid, 3-chloro-6-methoxyphenylacetic acid, 2-chloro-5-acetylphenylacetic acid, 2-chloro-4-hydroxyphenylacetic acid, 2,5-dichlorophenylacetic acid, 3-(2'-chlorophenyl) propanoic acid, 4-(4'-chlorophenyl) butanoic acid and also methyl, ethyl, n-propyl, isopropyl, n-butyl, isobutyl, n-octyl, benzyl, α-phenetyl or β-phenetyl esters thereof.

* * * * *